(12) United States Patent
Dede et al.

(10) Patent No.: US 7,595,039 B2
(45) Date of Patent: Sep. 29, 2009

US007595039B2

(54) METHODS OF HEALING WOUNDS BY ADMINISTERING HUMAN IL-18

(75) Inventors: Kimberly A. Dede, King of Prussia, PA (US); Judithann M. Lee, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 367 days.

(21) Appl. No.: 11/207,847

(22) Filed: Aug. 19, 2005

(65) Prior Publication Data

US 2006/0039892 A1 Feb. 23, 2006

Related U.S. Application Data

(60) Provisional application No. 60/603,012, filed on Aug. 20, 2004.

(51) Int. Cl.
*A61K 45/00* (2006.01)
*C07K 14/00* (2006.01)
(52) U.S. Cl. .................................. 424/85.2; 530/351
(58) Field of Classification Search ....................... None
See application file for complete search history.

(56) References Cited

U.S. PATENT DOCUMENTS

| | | | |
|---|---|---|---|
| 6,476,197 B1 * | 11/2002 | Yamamoto et al. .......... | 530/351 |
| 6,582,689 B1 | 6/2003 | Johnson | |
| 2004/0142037 A1 | 7/2004 | Engelmayer et al. | |
| 2005/0075277 A1 * | 4/2005 | Varadhachary et al. ......... | 514/6 |

FOREIGN PATENT DOCUMENTS

| WO | WO 2004/0024180 | 3/2004 |
|---|---|---|
| WO | WO 2004/0031276 | 4/2004 |

OTHER PUBLICATIONS

Kampfer H, et al. Lack of interferon-g production despite the presence of interleukin-18 during cutaneous wound healing. Molecular Medicine. 2000. vol. 6(12), pp. 1016-1027.*
Park J.E., et al. Understanding the role of immune regulation in wound healing. The American Journal of Surgery. 2004, vol. 187 (Suppl. to May 2004), p. 11S-16S.*

Abraham M, et al. The role of IL-18 and IL-12 in the modulation of matrix metalloproteinases and their tissue inhibitors in monocytic cells. International Immunology. 2002. vol. 14(12), p. 1449-1457).*
Armstrong D.G. et al. The role of matrix metalloproteinases in wound healing. (J. American Podiatric Medical Association. 2002. vol. 92(1), p. 12-18).*
Nold. M, et al. IL-18 initiates release of matrix metalloproteinase-9 from peripheral blood mononuclear cells without affecting tissue inhibitor of matrix metalloproteinases-1: suppression by TNFa blockage and modulation by IL-10. Naunyn-Schmiedeberg's Archives in Pharmacology. 2003. vol. 367, p. 68-75.*
Kämpfer, et al., "Counterregulation of Interleukin-18 mRNA and Protein Expression During Cutaneous Wound Repair in Mice," *Journal of Investigative Dermatology*, 1999, vol. 113(3), pp. 369-374.
Kämpfer, et al., "Regulation of Interleukin-18 (IL-18) Expression in Keratinocytes (HaCaT): Implications for Early Wound Healing," *European Cytokine Network*, 2000, vol. 11(4), pp. 626-633.
Puren, et al., "Interleukin-18 (IFNγ-inducing Factor) Induces IL-18 and IL-1β via TNFα Production from Non-CD14+ Human Blood Mononuclear Cells," *Journal of Clinical Investigation*, 1998, vol. 101(3), pp. 711-721.
Ushio, et al., "Cloning of the cDNA for Human IFN-γ-Inducing Factor, Expression in *Escherichia coli*, and Studies on Biologic Activities of the Protein," *Journal of Immunology*, 1996, vol. 156, pp. 4274-4279.
Bowen, et al., "New Pathways for Alimentary Mucositis," *Journal of Oncology*, vol. 2008, Article ID 907892, pp. 1-7, 2008.
McInnes, et al., "Interleukin-18: a therapeutic target in rheumatoid arthritis?," *Arthritis Research & Therapy*, vol. 7, No. 1, pp. 38-41, 2005.
Peterson, Douglas E., "Oral and Gastrointestinal Mucositis: Novel Insights into Pathophysiology and Potential Therapies," *Advanced Studies in Medicine*, vol. 5 (4B), pp. S299-S310, 2005.
Streit, et al., "Topical application of the tumour necrosis factor-α antibody infliximab improves healing of chronic wounds," *International Wound Journal*, vol. 3, No. 3, pp. 171-179, 2006.
Werner, et al., "Regulation of Wound Healing by Growth Factors and Cytokines," *Physiol. Rev.*, vol. 83, pp. 835-870, 2003.
U.S. Food and Drug Administration, Center for Drug Evaluation and Research, "Palifermin (marketed as Kepivance)," url document, 1 pp, 2004 updated 2007.

* cited by examiner

*Primary Examiner*—Robert Landsman
*Assistant Examiner*—Bruce D Hissong
(74) *Attorney, Agent, or Firm*—Elizabeth J. Hecht; William T. Han (57) ABSTRACT

The present invention relates generally to the use of human IL-18, also known as interferon-γ-inducing factor (IGIF), in the treatment of skin wounds, surgical wounds, leg ulcers, diabetic ulcers, gastrointestinal mucositis, oral mucositis, and lung injury.

5 Claims, 7 Drawing Sheets

Figure 1

Human IL-18 (SEQ ID NO:1)

| | | | | | | | | | | |
|---|---|---|---|---|---|---|---|---|---|---|
|YFGKL|ESKLS|VIRNL|NDQVL|FIDQG|NRPLF|EDMTD|SDCRD|NAPRT|IFIIS|50|
|MYKDS|QPRGM|AVTIS|VKCEK|ISTLS|CENKI|ISFKE|MNPPD|NIKDT|KSDII|100|
|FFQRS|VPGHD|NKMQF|ESSSY|EGYFL|ACEKE|RDLFK|LILKK|EDELG|DRSIM|150|
|FTVQN|ED|157| | | | | | | | |

Figure 2

Murine IL-18 (SEQ ID NO:2)

```
NFGRL HCTTA VIRNI NDQVL FVDKR QPVFE DMTDI DQSAS EPQTR LIIYM  50
YKDSE VRGLA VTLSV KDSKM STLSC KNKII SFEEM DPPEN IDDIQ SDLIF 100
FQKRV PGHNK MEFES SLYEG HFLAC QKEDD AFKLI LKKKD ENGDK SVMFT 150
LTNLH QS   157
```

Figure 3

Murine PDGF-β (AMINO ACIDS 1-61 AND 171-221 OF SEQ ID NO:3)

-20 MNRCWALFLP LCCYLRLVSA

1 EGDPIPEELY EMLSDHSIRS FDDLQRLLHR DSVDEDGAEL DLNMTRAHSG

51 VELESSSRGR RSLGSLAAAE PAVIAECKTR TEVFQISRNL IDRTNANFLV

101 WPPCVEVQRC SGCCNNRNVQ CRASQVQMRP VQVRKIEIVR KKPIFKKATV

151 TLEDHLACKC ETIVTPRPVT RSPGTSREQR AKTPQARVTI RTVRIRRPPK

201 GKHRKFKHTH DKAALKETLG A

Figure 4

Human KGF (SEQ ID NO:4)

```
  1    MCNDMTPEQM ATNVNCSSPE RHTRSYDYME GGDIRVRRLF CRTQWYLRID
 51    KRGKVKGTQE MKNNYNIMEI RTVAVGIVAI KGVESEFYLA MNKEGKLYAK
101    KECNEDCNFK ELILENHYNT YASAKWTHNG GEMFVALNQK GIPVRGKKTK
151    KEQKTAHFLP MAIT
```

Effect of daily topcial delivery of murine IL-18 protein on wound repair in ob/ob mice

SEQUENCE LISTING

<160> NUMBER OF SEQ ID NOS: 4

<210> SEQ ID NO 1
<211> LENGTH: 157
<212> TYPE: PRT
<213> ORGANISM: Homo sapien

<400> SEQUENCE: 1

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 2
<211> LENGTH: 157
<212> TYPE: PRT
<213> ORGANISM: Mus musculus

<400> SEQUENCE: 2

Asn Phe Gly Arg Leu His Cys Thr Thr Ala Val Ile Arg Asn Ile Asn
 1               5                  10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Asp Glu Asn Gly Asp
    130                 135                 140

Lys Ser Val Met Phe Thr Leu Thr Asn Leu His Gln Ser
145                 150                 155

```
<210> SEQ ID NO 3
<211> LENGTH: 241
<212> TYPE: PRT
<213> ORGANISM: Homo sapien
<220> FEATURE:
<221> NAME/KEY: SIGNAL
<222> LOCATION: (-241)...(20)

<400> SEQUENCE: 3

Met Asn Arg Cys Trp Ala Leu Phe Leu Pro Leu Cys Cys Tyr Leu Arg
-20             -15                 -10                 -5

Leu Val Ser Ala Glu Gly Asp Pro Ile Pro Glu Glu Leu Tyr Glu Met
                 1               5                  10

Leu Ser Asp His Ser Ile Arg Ser Phe Asp Asp Leu Gln Arg Leu Leu
         15                  20                  25

His Arg Asp Ser Val Asp Glu Asp Gly Ala Glu Leu Asp Leu Asn Met
         30                  35                  40

Thr Arg Ala His Ser Gly Val Glu Leu Glu Ser Ser Ser Arg Gly Arg
45                  50                  55                  60

Arg Ser Leu Gly Ser Leu Ala Ala Ala Glu Pro Ala Val Ile Ala Glu
                 65                  70                  75

Cys Lys Thr Arg Thr Glu Val Phe Gln Ile Ser Arg Asn Leu Ile Asp
             80                  85                  90

Arg Thr Asn Ala Asn Phe Leu Val Trp Pro Pro Cys Val Glu Val Gln
             95                 100                 105

Arg Cys Ser Gly Cys Cys Asn Asn Arg Asn Val Gln Cys Arg Ala Ser
        110                 115                 120

Gln Val Gln Met Arg Pro Val Gln Val Arg Lys Ile Glu Ile Val Arg
125                 130                 135                 140

Lys Lys Pro Ile Phe Lys Lys Ala Thr Val Thr Leu Glu Asp His Leu
                145                 150                 155

Ala Cys Lys Cys Glu Thr Ile Val Thr Pro Arg Pro Val Thr Arg Ser
                160                 165                 170

Pro Gly Thr Ser Arg Glu Gln Arg Ala Lys Thr Pro Gln Ala Arg Val
            175                 180                 185

Thr Ile Arg Thr Val Arg Ile Arg Arg Pro Pro Lys Gly Lys His Arg
        190                 195                 200

Lys Phe Lys His Thr His Asp Lys Ala Ala Leu Lys Glu Thr Leu Gly
205                 210                 215                 220

Ala

<210> SEQ ID NO 4
<211> LENGTH: 164
<212> TYPE: PRT
<213> ORGANISM: Mus musculus

<400> SEQUENCE: 4

Met Cys Asn Asp Met Thr Pro Glu Gln Met Ala Thr Asn Val Asn Cys
 1               5                  10                  15

Ser Ser Pro Glu Arg His Thr Arg Ser Tyr Asp Tyr Met Glu Gly Gly
                 20                  25                  30

Asp Ile Arg Val Arg Arg Leu Phe Cys Arg Thr Gln Trp Tyr Leu Arg
             35                  40                  45

Ile Asp Lys Arg Gly Lys Val Lys Gly Thr Gln Glu Met Lys Asn Asn
         50                  55                  60
```

-continued

```
Tyr Asn Ile Met Glu Ile Arg Thr Val Ala Val Gly Ile Val Ala Ile
 65              70                  75                  80

Lys Gly Val Glu Ser Glu Phe Tyr Leu Ala Met Asn Lys Glu Gly Lys
             85                  90                  95

Leu Tyr Ala Lys Lys Glu Cys Asn Glu Asp Cys Asn Phe Lys Glu Leu
            100                 105                 110

Ile Leu Glu Asn His Tyr Asn Thr Tyr Ala Ser Ala Lys Trp Thr His
        115                 120                 125

Asn Gly Gly Glu Met Phe Val Ala Leu Asn Gln Lys Gly Ile Pro Val
    130                 135                 140

Arg Gly Lys Lys Thr Lys Lys Glu Gln Lys Thr Ala His Phe Leu Pro
145                 150                 155                 160

Met Ala Ile Thr
```

METHODS OF HEALING WOUNDS BY ADMINISTERING HUMAN IL-18

CROSS-REFERENCE TO RELATED APPLICATION

This application claims priority to the earlier provisional U.S. application, Ser. No. 60/603,012, which was filed on Aug. 20, 2004, the contents of which are herein incorporated by reference in their entirety.

FIELD OF INVENTION

The present invention relates generally to the use of human IL-18, also known as interferon-γ-inducing factor (IGIF), in the treatment of wounds.

BACKGROUND OF THE INVENTION

The reason for this interest is the relative ease to target secreted protein therapeutics into their place of action (body fluids or the cellular membrane). Secreted proteins, and the extracellular regions of transmembrane proteins, can be directly administered into body fluids, or can be directed to body fluids or membranes by a natural pathway. The natural pathway for protein secretion into extracellular space is the endoplasmic reticulum in eukaryotes and the inner membrane in prokaryotes (Palade, *Science*, 189, 347 (1975); Milstein, et al., *Nature New Biol.*, 239, 117 (1972); Blobel, et al., *J. Cell. Biol.*, 67, 835 (1975)). On the other hand, there is no known natural pathway for exporting a protein from the exterior of the cells into the cytosol (with the exception of pinocytosis, a mechanism of snake venom toxin intrusion into cells). Therefore, targeting protein therapeutics into cells poses extreme difficulties in the art.

IL-18 is a recently discovered novel cytokine. Active human IL-18 contains 157 amino acid residues. It has potent biological activities, including induction of interferon-γ-production by T cells and splenocytes, enhancement of the killing activity of NK cells and promotion of the differentiation of naive CD4$^+$T cells into Th1 cells. In addition, human IL-18 augments the production of GM-CSF and decreases the production of IL-10. IL-18 has been shown to have greater interferon-γ inducing capabilities than IL-12, and appears to have different receptors and utilize a distinct signal transduction pathway.

CD4$^+$ T cells are the central regulatory elements of all immune responses. They are divided into two subsets, Th1 and Th2. Each subset is defined by its ability to secrete different cytokines. Interestingly, the most potent inducers for the differentiation are cytokines themselves. The development of Th2 cells from naive precursors is induced by IL-4. Prior to the discovery of IL-18, IL-12 was thought of as the principal Th1 inducing cytokine. IL-18 is also a Th1 inducing cytokine and is more potent than IL-12 in stimulating the production of interferon-γ.

Th1 cells secrete IL-2, interferon-γ, and TNF-β. Interferon-γ, the signature Th1 cytokine, acts directly on macrophages to enhance their microbiocidal and phagocytic activities. As a result, the activated macrophages can efficiently destroy intracellular pathogens and tumor cells. The Th2 cells produce IL-4, IL-5, IL-6, IL-10 and IL-13, which act by helping B cells develop into antibody-producing cells. Taken together, Th1 cells are primarily responsible for cell-mediated immunity, while Th2 cells are responsible for humoral immunity.

Wound repair is a highly orchestrated interplay involving several cell types, extracellular matrix components, and multiple soluble mediators, including growth factors and cytokines. Wound repair may be triggered by trauma, microbes or chemicals, which have caused tissue injury. Although restoration of tissue integrity is an innate host immune response, there are situations during which the wound repair process is impaired. Several growth factors have been used to try to prevent mucositis in cancer patients undergoing radiation or chemotherapy with limited success. Peterson, *Adv. Stud. Med.*, 4(4B): S299-S310, (2005). Granulocyte-colony stimulating factor (Neupogen) had a modest effect on the incidence and severity of mucositis in two out of four studies that involved cancer patients undergoing treatment. Granulocyte macrophage-colony stimulating factor (Sargramostim) induced a modest decrease in the severity of chemotherapy and radiation induced mucositis, although the results were inconsistent. Both granulocyte-colony stimulating factor and granulocyte macrophage-colony stimulating factor have only demonstrated an effect in the prevention of oral mucositis. Keratinocyte growth factor (Palifermin) has shown the most promise in the prevention of mucositis, preventing both the incidence and the duration of oral mucositis. With the emergence of agents that target mucositis pathophysiology, clinicians will no longer need to alter the radiation or chemotherapy regimens, but will tailor the protocol to include an agent that can prevent the incidence of mucositis. Clearly, there exists in the art a need to develop new therapeutic proteins to enhance wound repair, particularly to treat: skin wounds, surgical wounds, leg ulcers, diabetic ulcers, mucositis, particularly gastrointestinal mucositis and oral mucositis, and lung injury.

SUMMARY OF THE INVENTION

In one aspect, this invention provides a method of healing a wound in a patient in need thereof, comprising the step of administering to the patient a therapeutically effective amount of human IL-18 polypeptide (SEQ ID NO:1). In another aspect, the wound to be treated is chosen from the group of: skin wounds, surgical wounds, leg ulcers, diabetic ulcers, gastrointestinal mucositis, oral mucositis, and lung injury.

In a second aspect, this invention provides a method of healing such wounds in a patient in need thereof, comprising the step of administering to the patient a pharmaceutical composition comprising an effective amount of human IL-18 polypeptide (SEQ ID NO:1) and a carrier.

DESCRIPTION OF THE INVENTION

Human IL-18 polypeptides are disclosed in EP 0692536A2, EP 0712931A2, EP0767178A1, and WO 97/2441. The amino acid sequence of human IL-18 is set forth in SEQ ID NO:1. Human IL-18 polypeptides are interferon-γ-inducing polypeptides. They play a primary role in the induction of cell-mediated immunity, including induction of interferon-y production by T cells and splenocytes, enhancement of the killing activity of NK cells, and promotion of the differentiation of naive CD4+ T cells into Th1 cells.

IL-18 may be used to repair wounds in a patient, including, but not limited to: skin wounds, surgical wounds, leg ulcers, diabetic ulcers, pressure ulcers, mucositis, particularly gastrointestinal mucositis, and oral mucositis, and lung repair. Wound repair pertains to the regeneration of injured cells by cells of the same type. The process of wound repair involves the systematic coordination of the following cellular events: proliferation, migration, differentiation, and remodeling. Cytokines, chemokines, growth factors, and adhesion molecules function as cellular mediators, which orchestrate the particular cells involved in these activities. Kampfer, et al., *Molec. Med.* 6(12): 10160-1027 (2000). Interleukin-18 (IL-18), a pro-inflammatory cytokine, can induce Tumor Necrosis Factor-alpha, Interleukin 1-beta, and both CC and CXC chemokines, which may play a role during the inflammatory phase of the wound repair process. Puren, et al., *J. Clin. Invest.* 101: 711-721 (1998). Several different cell types have been identified that synthesize IL-18, including keratinocytes and activated macrophages, which both play a role in wound repair. In vitro cultures of Con A-stimulated peripheral blood mononuclear cells (PBMC) treated with human IL-18 have induced granulocyte monocyte-colony stimulating factor (GM-CSF) production. Ushio, et al., *J. Immunol.* 156: 4274-4279 (1996). Additionally, IL-18 has been shown to induce interferon-gamma (IFN-gamma) production by T-cells and NK cells. Granulocyte monocyte-colony stimulating factor has been shown to promote wound healing (Arnold, et al., *J. Wound Care* 54: 400-402 (1995)), and has been in the clinic to treat patients with chronic venous leg ulcers. DaCosta, et al., *Wound Rep. Reg.* 7: 17-25 (1999). In a murine excision model of wound repair, we have demonstrated that IL-18 promotes wound repair. The mechanism by which IL-18 promotes wound repair may be due to the pro-inflammatory nature of the cytokine, or as an inducing agent for growth factors like granulocyte monocyte-colony inducing factor.

Polypeptides of the present invention can be recovered and purified from recombinant cell cultures by well known methods, including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, and high performance liquid chromatography. Well known techniques for refolding proteins may be employed to regenerate active conformation when the polypeptide is denatured during intracellular synthesis, isolation and/or purification. Methods to purify and produce active human IL-18 are set forth in WO 01/098455.

The present invention also provides pharmaceutical compositions comprising human IL-18 polypeptides (SEQ ID NO:1). Such compositions comprise a therapeutically effective amount of a compound, and may further comprise a pharmaceutically acceptable carrier, diluent, or excipient. Such pharmaceutical carriers can be sterile liquids, such as water and oils, including those of petroleum, animal, vegetable or synthetic origin, such as peanut oil, soybean oil, mineral oil, sesame oil, etc. Water can be used as a carrier when the pharmaceutical composition is administered intravenously. Saline solutions and aqueous dextrose and glycerol solutions can also be employed as liquid carriers, for example, for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers, such as triglycerides. Oral formulation can include standard carriers, such as pharmaceutical grades of mannitol, lactose, starch, magnesium stearate, sodium saccharine, cellulose, magnesium carbonate, etc. Examples of suitable pharmaceutical carriers are described in REMINGTON'PHARMACEUTICAL SCIENCES by E. W. Martin. Such compositions will contain a therapeutically effective amount of the compound, often in purified form, together with a suitable amount of carrier so as to provide the form for proper administration to the patient. The formulation should suit the mode of administration.

In one embodiment of the invention, the composition is formulated in accordance with routine procedures as a pharmaceutical composition adapted for intravenous administration to human beings. Typically, compositions for intravenous administration are solutions in sterile isotonic aqueous buffer. Where suitable, the composition may also include a solubilizing agent and a local anesthetic, such as lignocaine, to ease pain at the site of the injection. Generally, the ingredients are supplied either separately or mixed together in unit dosage form, for example, as a dry lyophilized powder, or water-free concentrate, in a hermetically sealed container, such as an ampoule or sachette, indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Accordingly, the polypeptide may be used in the manufacture of a medicament. Pharmaceutical compositions of the invention may be formulated as solutions or as lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such a formulation is especially suitable for parenteral administration, but may also be used for oral administration or contained in a metered dose inhaler or nebulizer for insufflation. It may be desirable to add excipients, such as polyvinylpyrrolidone, gelatin, hydroxy cellulose, acacia, polyethylene glycol, mannitol, sodium chloride, or sodium citrate, to such pharmaceutical compositions.

Alternately, the polypeptide may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar, or gelatin. Liquid carriers include syrup, peanut oil, olive oil, saline, and water. The carrier may also include a sustained release material, such as glyceryl monostearate or glyceryl distearate, alone or with a wax. The amount of solid carrier varies but, will be between about 20 mg to about 1 g per dosage unit. The pharmaceutical preparations are made following the conventional techniques of pharmacy involving milling, mixing, granulating, and compressing, when suitable, for tablet forms; or milling, mixing and filling for hard gelatin capsule forms. When a liquid carrier is used, the preparation will be in the form of a syrup, elixir, emulsion, or an aqueous, or non-aqueous suspension. Such a liquid formulation may be administered directly by mouth (p.o.) or filled into a soft gelatin capsule.

Human IL-18 polypeptides may be prepared as pharmaceutical compositions containing an effective amount the polypeptide as an active ingredient in a pharmaceutically acceptable carrier. In the compositions of the invention, an aqueous suspension or solution containing the polypeptide, buffered at physiological pH, in a form ready for injection may be employed. The compositions for parenteral administration will commonly comprise a solution of the polypeptide of the invention or a cocktail thereof dissolved in a pharmaceutically acceptable carrier, such as an aqueous carrier. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the polypeptide of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g,. about 50 ng to about 30 mg, or from about 5 mg to about 25 mg, of a polypeptide of the invention. Similarly, a pharmaceutical composition of the invention for intravenous infusion could be made up to contain about 250 mL of sterile Ringer's solution, and about 1 mg to about 30 mg, or from about 5 mg to about 25 mg of a polypeptide of the invention. Actual methods for preparing parenterally administrable compositions are well known or will be apparent to those skilled in the art and are described in more detail in, for example, REMINGTON'PHARMACEUTICAL SCIENCE, 15th ed., Mack Publishing Company, Easton, Pa.

The polypeptides of the invention, when prepared in a pharmaceutical preparation, may be present in unit dose forms. The appropriate therapeutically effective dose can be determined readily by those of skill in the art. Such a dose may, if suitable, be repeated at appropriate time intervals selected as appropriate by a physician during the response period.

In addition, in vitro assays may optionally be employed to help identify optimal dosage ranges. The precise dose to be employed in the formulation will also depend upon the route of administration, and the seriousness of the disease or disorder, and should be decided according to the judgment of the practitioner and each patient's circumstances. Effective doses may be extrapolated from dose-response curves derived from in vitro or animal model test systems.

For polypeptides, the dosage administered to a patient is typically 0.1 mg/kg to 100 mg/kg of the patient's body weight. The dosage administered to a patient may be between 0.1 mg/kg and 20 mg/kg of the patient's body weight, or alternatively, 1 mg/kg to 10 mg/kg of the patient's body weight. Generally, human polypeptides have a longer half-life within the human body than polypeptides from other species, due to the immune response to the foreign polypeptides. Thus, lower dosages of human polypeptides and less frequent administration is often possible. Further, the dosage and frequency of administration of polypeptides of the invention may be reduced by enhancing uptake and tissue penetration (e.g., into the brain) of the polypeptides by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In another embodiment of the invention, a kit can be provided with the appropriate number of containers required to fulfill the dosage requirements for treatment of a particular indication.

In another embodiment, the compound or composition can be delivered in a vesicle, in particular a liposome (see Langer, Science 249:1527-1533 (1990); Treat, et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, *CRC Crit. Ref. Biomed. Eng.* 14:201 (1987); Buchwald, et al., *Surgery* 88:507 (1980); Saudek, et al., *N. Engl. J. Med.* 321: 574 (1989)). In another embodiment, polymeric materials can be used (see MEDICAL APPLICATIONS OF CONTROLLED RELEASE, Langer and Wise (eds.), CRC Pres., Boca Raton, Fla. (1974); CONTROLLED DRUG BIO-AVAILABILITY, DRUG PRODUCT DESIGN AND PERFORMANCE , Smolen and Ball (eds.), Wiley, New York (1984); Ranger, et al., *J., Macromol. Sci. Rev. Macromol. Chem.* 23:61 (1983); see also Levy, et al., *Science* 228:190 (1985); During, et al., *Ann. Neurol.* 25:351 (1989); Howard, et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in MEDICAL APPLICATIONS OF CONTROLLED RELEASE , supra, vol. 2, pp. 115-138 (1984)). Other controlled release systems are discussed in the review by Langer (*Science* 249: 1527-1533 (1990)).

Human IL-18 polypeptides (SEQ ID NO:1) may be administered by any appropriate internal route, and may be repeated as needed, e.g., as frequently as one to three times daily for between 1 day to about three weeks to once per week or once biweekly. Alternatively, the peptide may be altered to reduce charge density and thus allow oral bioavailability. The dose and duration of treatment relates to the relative duration of the molecules of the present invention in the human circulation, and can be adjusted by one of skill in the art, depending upon the condition being treated and the general health of the patient.

The invention provides methods of treatment, inhibition and prophylaxis by administration to a human patient an effective amount of a compound or pharmaceutical composition of the invention comprising human IL-18 polypeptide (SEQ ID NO:1). In one embodiment of the invention, the compound is substantially purified (e.g., substantially free from substances that limit its effect or produce undesired side-effects). Formulations and methods of administration can be employed when the compound comprises a polypeptide as described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu, et al., *J. Biol. Chem.* 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In one embodiment of the invention, it may be desirable to administer the pharmaceutical compounds or compositions of the invention locally to the area in need of treatment. Such administration may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. When administering a protein, it is advisable to use materials to which the protein does not absorb.

The mode of administration of a polypeptide of the invention may be any suitable route that delivers the agent to the host. The polypeptides and pharmaceutical compositions of the invention are particularly useful for parenteral administration, i.e., subcutaneously, intramuscularly, intravenously or intranasally, or for topical administration, if used to repair a wound on the skin. To treat mucositis, the polypeptides can be delivered to the patient via parenteral administration.

The present invention may be embodied in other specific forms, without departing from the spirit or essential attributes thereof, and, accordingly, reference should be made to the appended claims, rather than to the foregoing specification or following examples, as indicating the scope of the invention.

Glossary

The following definitions are provided to facilitate understanding of certain terms used frequently hereinbefore.

As used herein, the term, "carrier", refers to a diluent, adjuvant, excipient, or vehicle with which the therapeutic is administered.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from at least one of its coexisting cellular materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

The term, "mucositis", as used herein, means the destruction of the epithelial lining of an organ, e.g., in the intestine, bladder, mouth, resulting from irradiation or chemotherapy.

As used herein, the term, "pharmaceutical", includes veterinary applications of the invention. The term, "therapeutically effective amount", refers to that amount of therapeutic agent, which is useful for alleviating a selected condition.

As used herein, the term, "pharmaceutically acceptable", means approved by a regulatory agency of the Federal or a state government or listed in the U.S. Pharmacopeia or other generally recognized pharmacopeia for use in animals, and more particularly in humans. "Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins, such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, 1-12, in POST TRANSLATIONAL COVALENT MODIFICATION OF PROTEINS, B. C. Johnson, Ed., Academic Press, New York, 1983; Seifter et al., *Meth Enzymol,* 182, 626-646, 1990; Rattan, et al., *Ann. NY Acad. Sci.,* 663: 48-62 (1992)).

Covalent attachment of biologically active compounds to water-soluble polymers is one method for alteration and control of biodistribution, pharmacokinetics, and often, toxicity for these compounds (Duncan, R. and Kopecek, J. (1984) *Adv. Polym. Sci.* 57:53-101). Many water-soluble polymers have been used to achieve these effects, such as poly(sialic acid), dextran, poly(N-(2-hydroxypropyl)methacrylamide) (PHPMA), poly(N-vinylpyrrolidone) (PVP), poly(vinyl alcohol) (PVA), poly(ethylene glycol-co-propylene glycol), poly(N-acryloyl morpholine (PAcM), and poly(ethylene glycol) (PEG) (Powell, G. M. (1980) Polyethylene glycol. In R. L. Davidson (Ed.) HANDBOOK OF WATER SOLUBLE GUMS AND RESINS. McGraw-Hill, New York, chapter 18). PEG possess an ideal set of properties: very low toxicity (Pang, S. N. J. (1993) *J. Am. Coll. Toxicol.* 12: 429-456) excellent solubility in aqueous solution (Powell, supra), low immunogenicity and antigenicity (Dreborg, S. and Akerblom, E. B. (1990) Crit. *Rev. Ther. Drug Carrier Syst.* 6: 315-365). PEG-conjugated or "PEGylated" protein therapeutics, containing single or multiple chains of polyethylene glycol on the protein, have been described in the scientific literature (Clark, R., et al. (1996) *J. Biol. Chem.* 271: 21969-21977; Hershfield, M. S. (1997) Biochemistry and immunology of poly(ethylene glycol)-modified adenosine deaminase (PEG-ADA). In J. M. Harris and S. Zalipsky (Eds) Poly (ethylene glycol): Chemistry and Biological Applications. American Chemical Society, Washington, D.C., p 145-154; Olson, K., et al. (1997) Preparation and characterization of poly(ethylene glycol)ylated human growth hormone antagonist. In J. M. Harris and S. Zalipsky (Eds) Poly(ethylene glycol): Chemistry and Biological Applications. American Chemical Society, Washington, D.C., p 170-181).

As used herein, the term, "wound repair", means the tissue repair processes involved in healing a wound, including, but not limited to, wound closure.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLE 1

Excisonal Wound Repair Model

Diabetic mice, such as the ob/ob strain, display delayed wound healing. Stallmeyer, et al., *Diabetologia* 44: 471-479 (2001). Ob/ob mice are a naturally occurring strain of mice that have a deletion of the ob/ob gene, which codes for leptin. Leptin binds to a cytokine class I receptor, obRb, and activates the intracellular signaling cascade that curtails appetite. Because the ob/ob mice cannot produce leptin, they are obese, being twice the weight of a normal C57/B16 mouse. The obese mice also have other metabolic defects, including reduced thermogenesis, hyperphagia, decreased fertility, and inhibition of growth hormone. Ring, et al., *Endocrinol.* 141 (1): 446-449 (2000). The pronounced retardation on wound healing in ob/ob mice has been attributed to their diabetic-like phenotype.

Models of impaired wound healing permit the opportunity to explore the effect of specific cytokines, such as IL-18, and growth factors, such as Platelet-Derived Growth Factor (PDGF), on wound repair. Topical application of PDGF-β has been shown to enhance wound healing in the diabetic mouse strain, db/db. Greenlaugh, et al., *Am. J. Pathol.* 136: 1235-1246 (1990). The db/db strain is phenotypically similar to the ob/ob strain, but the db/db mice lack the leptin receptor. The wounds of db/db mice exhibit a marked delay in cellular infiltration, granualtion tissue formation, and delayed wound healing. Platelet-derived growth factor (PDGF-β) is both a mitogen and a chemoattractant for smooth muscle cells and fibroblasts, and caused rapid re-epithelialization of wounds in db/db mice. Although Interleukin-18 (IL-18) has not been used previously as a therapeutic agent in a wound healing model, studies have shown the increased expression levels, but not protein production, of IL-18 in wounds of ob/ob mice. Kampfer, et al., *J. Invest. Derm.* 113(3): 369-74 (1999). Because IL-18 is a pro-inflammatory cytokine (Kampfer, et al., *Eur. Cytokine Netw.* 11: 626-33 (2000)), it may play a role in wound healing by stimulating the cellular infiltrate into the wounds.

To determine the effect of topical delivery of IL-18 or PDGF-β on wound repair, ten to fourteen week old female ob/ob mice were anesthesitized using a Ketamine (90 mg/kg)/Xylazine (10 mg/kg) cocktail. Adenoviral-mediated over-expression of PDGF was shown to correct ischemic wound healing in a rabbit ear model. Liechty, et al., *J. Invest. Dermatol.* 113:375-383 (1999). Liechty, et al. demonstrated that replication deficient adenovirus efficiently delivered the PDGF-β transgene directly to cells in the wounded area. The upper back of each mouse was shaved, and a sterile field was established using alternate wipes of alcohol and Betadine. Full-thickness circular excisional wounds 6 mm in diameter were created using a sterile biopsy punch, resulting in two wounds per mouse. For topical delivery, adenovirus ($1 \times 10^{10}$ viral particles/wound) coding for a murine IL-18 (SEQ ID NO:2), murine PDGF-β (amino acids 1-61 and 171-221 of SEQ ID NO:3), or a control (empty adenovirus-CMV.Null)) was applied directly onto the wounded area. A saline control was also directly applied to the wounds. Polaxamer (Pluronic F127 in 10% phosphate buffered saline (PBS)) was subsequently overlaid onto the wounds, which were then covered with a transparent sterile dressing. To determine the rate of wound closure, the circumference of the wounds was traced onto transparency film at two day intervals. At the end of the study when all the wounds had healed, the transparency films were optically scanned, and the surface area was determined using Scion Image software (Scion Corporation, Frederick, Md., U.S.A.). The results of this experiment appear below in FIG. 5.

The control adenovirus, Ad.mPDGF-β (amino acids 1-61 and 171-221 of SEQ ID NO:3), was generated by using a direct cloning approach (Sukmanm A. J., Kallarakal, A., Fornwald, J., Kozarsky, K. F., Appelbaum, E., Shatzman, A. R., and Lu, Q. 2002. Generation of recombinant adenovirus vectors by a direct cloning approach. In Gene Cloning and Expression Technologies, M. P. Weiner and Q. Lu (Eds.). p 341-355. Eaton Publishing, Westborough, Mass.). Briefly, the ORF for murine PDGF-β was PCR amplified and cloned into the XbaI/SwaI sites of pAC2XS, placing the gene under the control of CMV IE promoter. The purified molecular clone DNA of adenovirus vector was linearized by digesting with restriction enzyme PacI to expose ITRs, and transfected into HEK293 cells for adenovirus rescue. The adenovirus was amplified and purified by CsCl banding as described (Engelhardt, J. 1999. Methods for adenovirus-mediated gene transfer to airway epithelium. In Methods in Molecular Medicine, Gene Therapy Protocols, P. Robbins (Ed.). p. 169-184. Humana Press, Totowa). Concentrated adenovirus was desalted by using a Bio-gel column (Bio-Rad) and stored in 1×PBS with 10% glycerol at −80° C. The Ad.m-IL-18 construct was generated using the methods described in Osaki, et al., *Gene Therapy* 6: 808-815 (1999).

Figure 1:
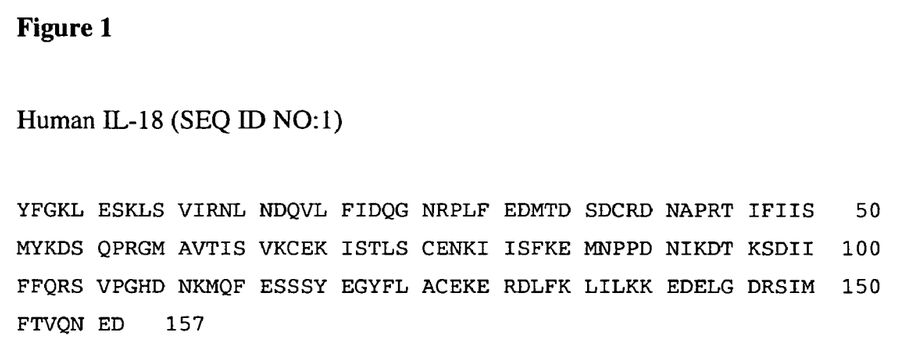
FIG. 1 shows the amino acid sequence of native human IL-18 (SEQ ID NO:1).
Figure 2:
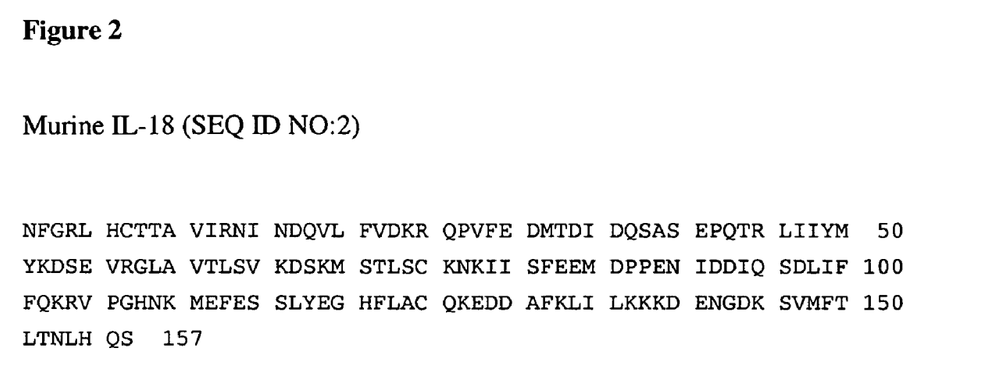
FIG. 2 shows the amino acid sequence of murine IL-18 (SEQ ID NO:2).
Figure 3:
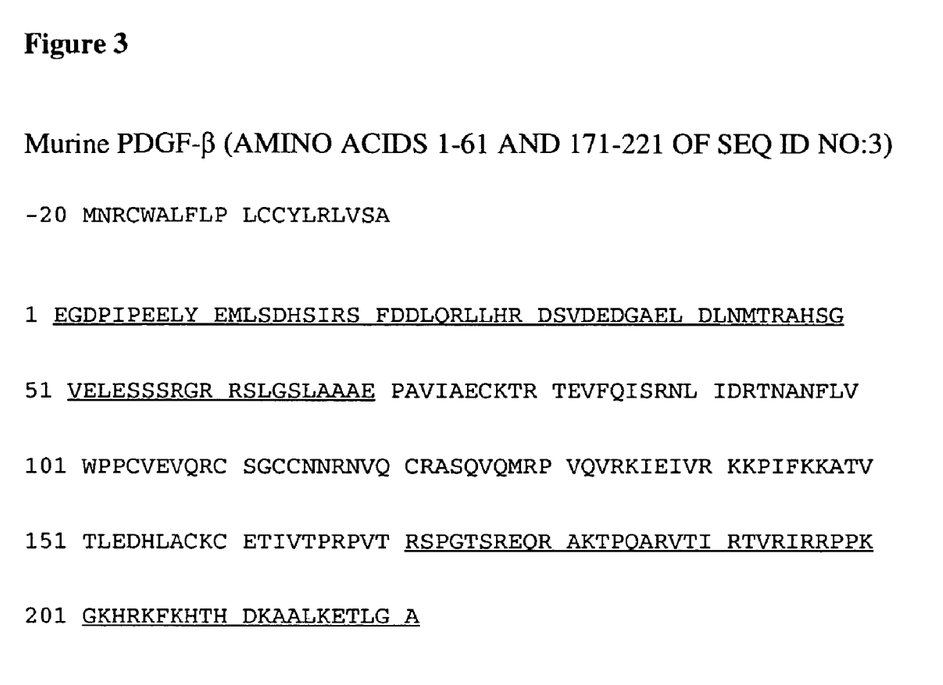
FIG. 3 shows the amino acid sequence of murine platelet derived growth factor-β (PDGF-β) (SEQ ID NO:3). Mature mouse PDGF-β is formed by removal of a signal peptide (−20−−1) and both N-terminal (1-61) and C-terminal (171-221) propeptides (underlined).
Figure 4:
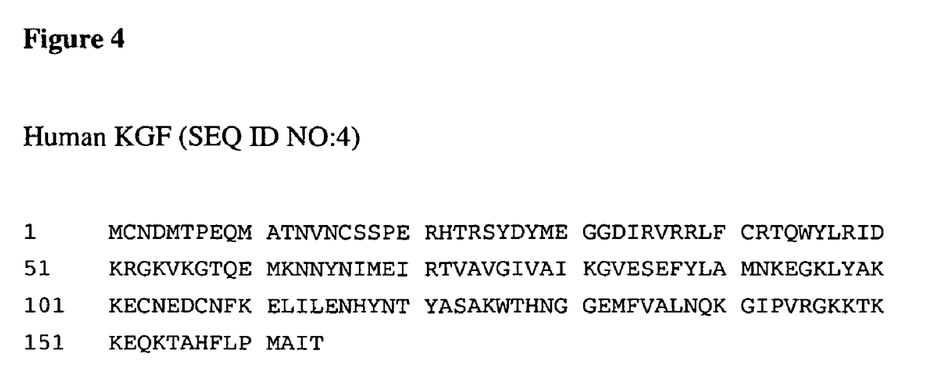
FIG. 4 shows the amino acid sequence of human KGF (SEQ ID NO:4).
Figure 5:
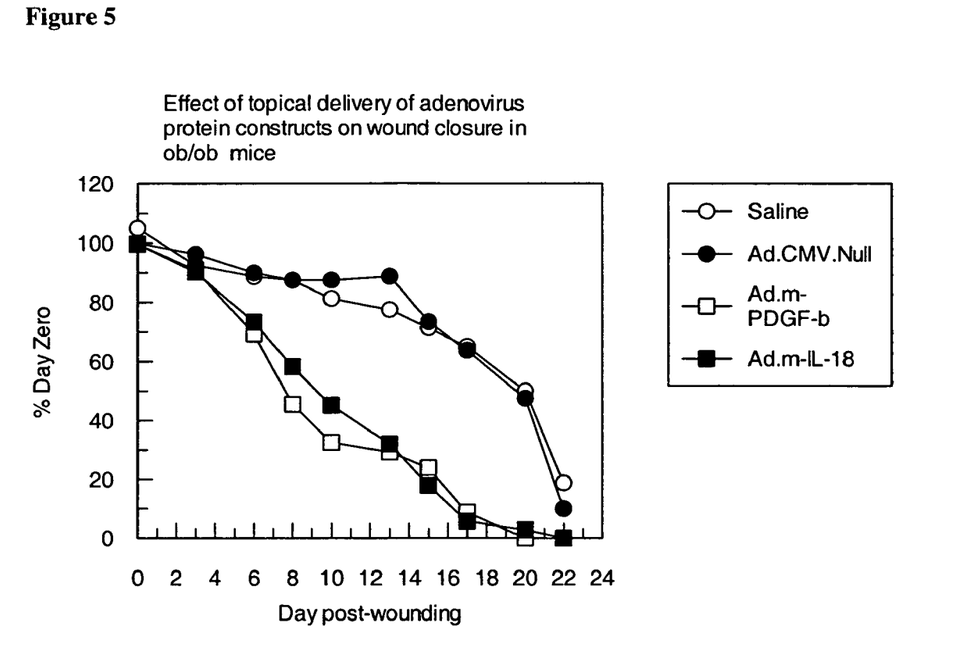
FIG. 5 shows the effect of topical administration of murine IL-18 (SEQ ID NO:2) encoded into adenovirus on wound repair in ob/ob mice. Each data point represents the mean for each treatment group.

For the topical delivery of the protein constructs in an adenovirus vector, both Ad.m-PDGF-β (amino acids 1-61 and 171-221 of SEQ ID NO:3) and Ad.m-IL-18 (SEQ ID NO:2) greatly enhanced wound closure in the ob/ob excisional wound repair model. Ad.m-PDGF-β (amino acids 1-61 and 171-221 of SEQ ID NO:3), the positive control protein, and Ad.m-IL-18 (SEQ ID NO:2) reached 50% Day Zero closure on day 7.5 and 9.5, respectively, versus the vector control (Ad.CMV.Null), which achieved 50% Day Zero closure on day 20 post-wounding. Additionally, the Ad.m-IL-18 (SEQ ID NO:2) and Ad.m-PDGF-β (amino acids 1-61 and 171-221 of SEQ ID NO:3) both accelerated the full closure of the wounds by day 20. At the time of the conclusion of the study on day 22 post-wounding, neither the saline nor the vector control groups had fully healed. Having demonstrated the positive effect of topically applied Ad.IL-18 in the excisional wound repair model, the systemic delivery of murine IL-18 protein (SEQ ID NO:2) was tested.

To determine the effect of systemic delivery of murine IL-18 (SEQ ID NO:2), ten to fourteen week old female ob/ob mice were anesthesitized using a Ketamine (90 mg/kg)/Xylazine (10 mg/kg) cocktail. Two hours prior to the wounding procedure, the mice were given intra-peritoneal injections of the murine IL-18 protein (SEQ ID NO:2) at multiple concentrations (0.1 µg/0.5 ml to 100 µg/0.5 ml) or the vehicle (PBS without calcium and magnesium). The upper back of the mouse was shaved, and a sterile field was established using alternate wipes of alcohol and Betadine. Full-thickness circular excisional wounds 6 mm in diameter were created using a sterile biopsy punch, resulting in two wounds per mouse. Saline was applied directly onto the wounds, which were then covered with a transparent sterile dressing. To determine the rate of wound closure, the circumference of the wounds were traced onto transparency film at two day intervals. At the end of the study when all the wounds had healed, the transparency films were optically scanned, and the surface area was determined using Scion Image software (Scion Corporation, Frederick, Md., U.S.A.). Throughout the duration of the systemic studies, mice were monitored for weight loss or gain. The results from this experiment appear below in FIG. 6.

Figure 6:
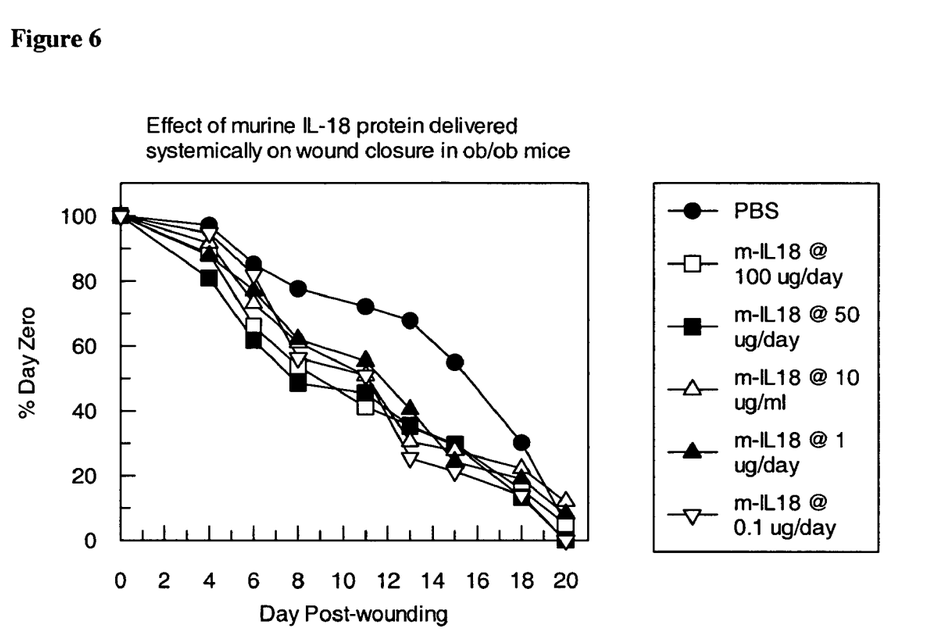
FIG. 6 shows the effect of murine IL-18 purified protein (SEQ ID NO:2) delivered daily systemically by intraperitoneal injection on wound repair in ob/ob mice. Each data point represents the mean for each treatment group.

For the systemic delivery of the purified protein, murine IL-18 (SEQ ID NO:2) enhanced the rate of wound closure in a dose-dependent manner, over a dose range of 0.1 µg to 100 µg/mouse/day. The most effective doses were 50 and 100 µg/mouse/day, which reached 50% Day Zero closure by day 8 and 9, respectively, versus the vehicle control, which achieved 50% Day Zero closure by day 16. The rate of full closure was increased for the m-IL-18 (SEQ ID NO:2) treatments relative to the PBS control.

Both topically and systemically delivered murine IL-18 (SEQ ID NO:2) enhanced wound closure in the ob/ob excisional model of wound repair. PDGF was used as the positive control in our murine wound repair studies. Recombinant human platelet-derived growth factor was approved by the U.S. Food and Drug Administration for the treatment of diabetic foot ulcers. Wieman, et al. *Am. J. Surg.* 176:745-795 (1998). Many physical maladies are caused by tissue injuries, which disrupt the natural organization of the tissue, resulting in a wound. The indications claimed in this patent are all examples of tissue insults, which could be repaired by treatment with human IL-18 (SEQ ID NO:1).

EXAMPLE 2

Topical Daily Application of Human IL-18 to an Excisional Wound

Figure 7:
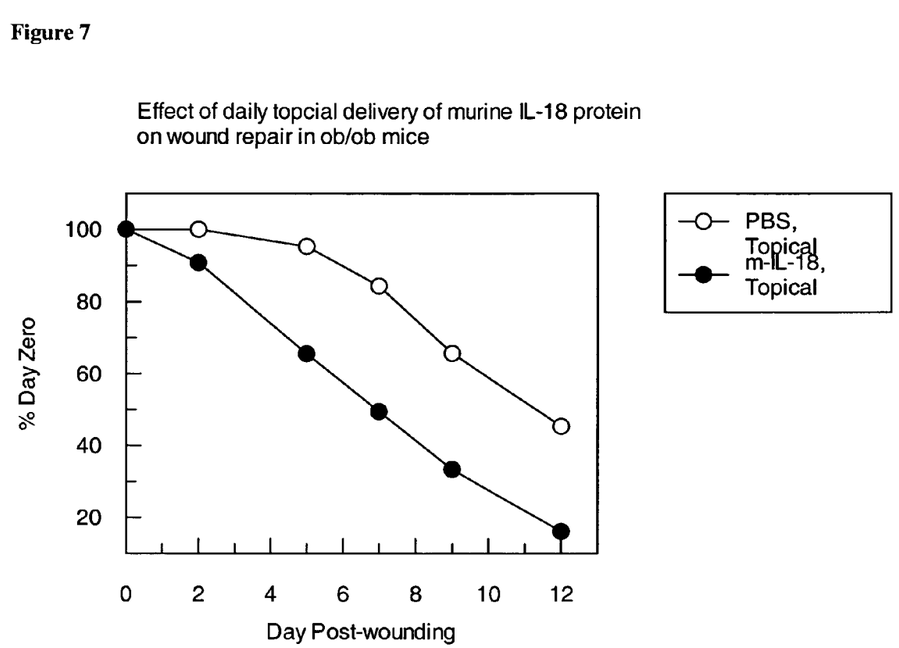
FIG. 7 shows the effect of daily topical delivery of human IL-18 (SEQ ID NO:1) on wound repair in ob/ob mice. Each data point represents the mean for each treatment group.

Since murine IL-18 (SEQ ID NO:2) was effective in the murine excisional wound repair model when delivered topically as an adenovirus construct, a study was performed using purified human IL-18 (SEQ ID NO:1) protein applied daily directly onto the wound from Example 1, above. Human IL-18 protein (SEQ ID NO:1) was applied as 10 µg/30 µl/wound. Phosphate Buffered Saline (PBS) was used as the diluent control. The results appear in FIG. 7 below, which show that human IL-18 (SEQ ID NO:1) accelerated wound repair relative to the PBS control. In the clinic, human PDGF has been used topically to treat diabetic foot ulcers. Wieman et al. *Am. J. Surg.* 176:745-795 (1998).

EXAMPLE 3

Intestinal Mucositis Model

Cancer therapies, such as chemotherapy or radiation, often result in cytotoxic damage to the gastrointestinal tract by destruction of the crypts. This crypt loss causes ulcers to develop along the denuded areas of epithelium, causing gastrointestinal mucositis. A closely related condition, oral mucositis, occurs when the epithelial lining of the mouth is damaged by cytotoxic agents, causing ulcers to develop. If a protein, such as human Keratinocyte Growth Factor (KGF) (SEQ ID NO:4), is active in the intestinal mucositis model, it may act as a mitogenic factor, by stimulating the proliferation and differentiation of the epithelium. Potten, et al., *Cell Growth Differ.* 12: 265-75 (2001). Alternatively, human KGF (SEQ ID NO:4) could act as a cell cycle inhibitor that induces stem cell arrest prior to the cytotoxic insult, thereby protecting the stem cells, which in turn, prolong crypt survival. Farrell, et al., *Cancer Res.* 58: 933-39 (1998). Similarly, in oral mucositis, therapies that reduce the sensitivity of the stem cells to cytotoxic insult and/or improve the regenerative response post exposure will have a clinical impact by reducing the side-effects of current cancer treatment protocols. Sonis, et al., *J. Am. Dent. Assoc.* 97: 468-472 (1978).

One assay protocol was employed to address the role of IL-18 in mucositis: the crypt survival assay.

A. Crypt Survival Assays—Model of Intestinal Mucositis

The protocol described below was adapted from EpiStem, Ltd., Incubator Building, Grafton Street, Manchester, M13 9XX, UK.

Used 30 adult (10-12 week-old) male BDF1 mice. All were housed for 2 weeks to stabilise the circadian rhythm (Potten, et al., 1977, *Cell Tissue Kinet.*, 10, 557). Mice were held in individually ventilated cages (IvCs) in an SPF barrier unit on a 12 hour light:dark cycle. Animals were allowed food and water ad libitum throughout. All procedures were certified according to the UK Home Office (Animal Procedures) Act 1986. Animals were randomised 6 per group, between the following 6 groups: (1) saline injected ip, pre- and post-irradiation; (2) drug injected ip pre- and saline injected post-irradiation; (3) saline injected ip pre- and drug injected post-irradiation; (4) drug injected pre- and post-irradiation; (5) untreated controls; and (6) human KGF (SEQ ID NO:4) injected ip pre-and saline injected post-irradiation (positive control).

Intestinal damage was induced using a single dose of 13Gy X-ray irradiation, whole body exposure. 13Gy was the best mid-range dose to start with, as it should have picked up any potential protective effects of a test compound (Withers, et al., 1969, *Rad. Res.*, 38, 598). All animals were weighed once daily from initiation of treatment to the time of sacrifice. Animals were sacrificed 4 days post-irradiation. The small intestine was removed and fixed in Carnoy's fixative. All tissue was processed for histology (paraffin embedded). Using the Carnoy's-fixed material the number of surviving intestinal crypts in each treatment group was scored and size-corrected using an untreated control, as per "Clono-Quant™". For each mouse, 10 cross-sections of intestine were scored and the average number of crypts per cross-section was measured (Farrell, et al., 1998, *Cancer Res.*, 58, 933). The crypt widths were also measured to correct for scoring errors, due to size. After size correction the mean number of crypts per cross-section, per group was be scored. The injection protocol that was used appears below in Table 1. The protein was purchased from PeproTech, catalogue number 100-19.

TABLE 1

| Gp | −3 | −2 | −1 | 0 | 0 | +1 | +2 | +3 | +4 |
|---|---|---|---|---|---|---|---|---|---|
| 1 | S | S | S | S | I | S | S | S | C |
| 2 | D | D | D | D | I | S | S | S | C |
| 3 | S | S | S | S | I | D | D | D | C |
| 4 | D | D | D | D | I | D | D | D | C |
| 5 |   |   |   |   |   |   |   |   | C |
| 6 | KGF | KGF | KGF | KGF | I | S | S | S | S |

S = Saline intraperitoneal injection
D = Drug intraperitoneal injection
KGF = Positive control intraperitoneal injection
I = Irradiate with 13Gy
C = Cull
Gp = Group For this protocol, all injections were given at 09:00 hours. The irradiation was carried out at 15:00 hours.

The effect of murine IL-18 (SEQ ID NO:2) on intestinal crypt survival following irradiation was determined in study 04/135C, which was performed under contract by EpiStem Ltd. EpiStem's CLONOQUANT® system identified and quantified the regenerating crypts in transverse sections of the small intestine. Following the cytotoxic insult, the regenerating crypts rapidly proliferated and were easily distinguished from dying crypts. Human KGF (SEQ ID NO:4) was dosed at 6.25 mg/kg/day and was run as the positive control in the study. Murine IL-18 (SEQ ID NO:2) was dosed at 5 mg/kg/day. Data for the number of surviving crypts per crypt circumference are reported below in FIG. 6.

Table 2, below, summarizes the data from the radiation-induced mucositis model. The positive control for the radiation-induced mucositis study, human KGF (SEQ ID NO:4), demonstrated good activity when dosed three days prior to irradiation. The human KGF (SEQ ID NO:4) group showed a fourfold increase in the number of surviving crypts relative to the saline control group. Murine IL-18 (SEQ ID NO:2) had comparable activity to human KGF (SEQ ID NO:4) when dosed three days prior to irradiation, showing a threefold increase in crypt survival. When murine IL-18 (SEQ ID NO:2) was dosed both pre- and post-irradiation, the number of crypts surviving relative to the saline control was increased twofold. Dosing murine IL-18 (SEQ ID NO:2) post-irradiation only was the least effective, resulting in only a 1.6-fold increase in surviving crypts. Thus, three-day dosing of murine IL-18 (SEQ ID NO:2) prior to irradiation was the most effective regimen.

Although chemotherapy and radiotherapy may be successful treatments for killing cancerous cells, healthy tissue is often destroyed, as well. When the epithelial lining of the gastrointestinal tract is compromised, ulceration and crypt destruction can occur, leaving the patient in pain, unable to eat and susceptible to infection. Additionally, the development of mucositis can lead to lack of compliance of the patient in the completion of the full regimine of radiotherapy or chemotherapy. In murine models, KGF ameliorated radiation and chemotherapy-induced injury of oral and gastrointestinal tract epithelium. Recombinant [human] KGF has been shown to reduce oral mucositis in patients with metastatic colorectal cancer receiving fluorouracil plus leucovorin. Meropol et al. *J. Clin. Oncol.* 21:1452-1458 (2003). In the irradiation-induced mucositis model, murine IL-18 (SEQ ID NO:2) has shown efficacy in the protection of intestinal crypts, and could be used as a palliative treatment in humans. Since IL-18 has shown a positive effect in treating radiation-induced mucositis, it may also heal the damaged epithelium evident in oral mucositis.

TABLE 2

RAW DATA: NUMBER OF SURVIVING CRYPTS PER CRYPT CIRCUMFERENCE

| Treatment | mouse 1 | mouse 2 | mouse 3 | mouse 4 | mouse 5 | mouse 6 | Mean |
|---|---|---|---|---|---|---|---|
| saline pre-irrad and post-irrad | 1.4 | 4.9 | 8 | 3.9 | 3.1 | 5 | 4.4 |
| KGF pre-irrad | 17.2 | 12.4 | 10.3 | 20.3 | 24.2 | 23.1 | 17.9 |
| IL-18 pre-irrad | 21 | 11 | 10 | 6.1 | 9.6 | 21 | 13 |
| IL-18 post-irrad | 8 | 5.6 | 9.8 | 3.5 | 47 | 10.6 | 7 |
| IL-18 pre and post-irrad | 10.5 | 11.4 | 10.5 | 8 | 8.6 | 5.2 | 9 |
| Untreated, non irrad controls | 105.1 | 100.3 | 107.6 | 102.4 | 105.5 | 105.5 | 104.4 | irrad = irradiated

What is claimed is:

1. A method of treating a wound in a patient, wherein the wound is chosen from the group consisting of: mucositis, diabetic ulcers, and skin wounds, said method comprising the step of administering to the patient a therapeutically effective amount of human IL-18 polypeptide (SEQ ID NO:1) in combination with a pharmaceutically acceptable carrier.

2. The method as claimed in claim 1, wherein the human IL-18 is administered via parenteral administration.

3. The method as claimed in claim 2, wherein the parenteral administration is chosen from the group consisting of: subcutaneous, intramuscular, intravenous, and intranasal administration.

4. The method as claimed in 1 wherein the mucositis is oral mucositis.

5. The method as claimed in claim 1, wherein the mucositis is intestinal mucositis.

* * * * *